(12) United States Patent
Blackwood et al.

(10) Patent No.: US 8,134,124 B2
(45) Date of Patent: Mar. 13, 2012

(54) METHOD FOR CREATING S/TEM SAMPLE AND SAMPLE STRUCTURE

(75) Inventors: Jeff Blackwood, Portland, OR (US); Stacey Stone, Beaverton, OR (US)

(73) Assignee: FEI Company, Hillsboro, OR (US)

( * ) Notice: Subject to any disclaimer, the term of this patent is extended or adjusted under 35 U.S.C. 154(b) by 367 days.

(21) Appl. No.: 12/446,420

(22) PCT Filed: Oct. 22, 2007

(86) PCT No.: PCT/US2007/082159
§ 371 (c)(1),
(2), (4) Date: Jun. 16, 2009

(87) PCT Pub. No.: WO2008/051937
PCT Pub. Date: May 2, 2008

(65) Prior Publication Data
US 2010/0300873 A1 Dec. 2, 2010

Related U.S. Application Data

(60) Provisional application No. 60/853,183, filed on Oct. 20, 2006.

(51) Int. Cl.
*G01N 1/28* (2006.01)
*G01R 31/305* (2006.01)
(52) U.S. Cl. ...... 250/304; 250/307; 250/311; 250/491.1
(58) Field of Classification Search .................. 250/304, 250/307, 311, 491.1, 492
See application file for complete search history.

(56) References Cited

U.S. PATENT DOCUMENTS

| | | | |
|---|---|---|---|
| 5,270,552 A | 12/1993 | Ohnishi et al. |
| 5,315,123 A | 5/1994 | Itoh et al. |
| 5,656,811 A | 8/1997 | Itoh et al. |
| 5,847,821 A | 12/1998 | Tracy et al. |
| 5,942,805 A | 8/1999 | Winer et al. |
| 6,039,000 A | 3/2000 | Libby et al. |
| 6,188,072 B1 | 2/2001 | Chung |

(Continued)

FOREIGN PATENT DOCUMENTS
EP 1204133 5/2002
(Continued)

OTHER PUBLICATIONS

Giannuzzi, Lucille A., et al., 'FIB Lift-Out for Defect Analysis,' Microelectronic Failure Analysis: Desk Reference, Nov 2002, pp. 29-35.

(Continued)

*Primary Examiner* — Jack Berman
(74) *Attorney, Agent, or Firm* — Scheinberg & Griner, LLP; Michael O. Scheinberg; David Griner

(57) ABSTRACT

An improved method and apparatus for S/TEM sample preparation and analysis. Preferred embodiments of the present invention provide improved methods for TEM sample creation, especially for small geometry (<100 nm thick) TEM lamellae. A novel sample structure and a novel use of a milling pattern allow the creation of S/TEM samples as thin as 50 nm without significant bowing or warping. Preferred embodiments of the present invention provide methods to partially or fully automate TEM sample creation, to make the process of creating and analyzing TEM samples less labor intensive, and to increase throughput and reproducibility of TEM analysis.

25 Claims, 15 Drawing Sheets

U.S. PATENT DOCUMENTS

| | | |
|---|---|---|
| 6,420,722 B2 | 7/2002 | Moore et al. |
| 6,497,194 B1 | 12/2002 | Libby et al. |
| 6,521,890 B2 | 2/2003 | Ishitani et al. |
| 6,538,254 B1 | 3/2003 | Tomimatsu et al. |
| 6,570,170 B2 | 5/2003 | Moore |
| 6,573,516 B2 | 6/2003 | Kawakami |
| 6,576,900 B2 | 6/2003 | Kelly et al. |
| 6,593,583 B2 | 7/2003 | Iwasaki |
| 6,608,920 B1 | 8/2003 | Su et al. |
| 6,681,039 B1 | 1/2004 | Roberts et al. |
| 6,717,156 B2 | 4/2004 | Koike et al. |
| 6,781,125 B2 | 8/2004 | Tokuda et al. |
| 6,841,788 B1 | 1/2005 | Robinson et al. |
| 6,842,538 B2 | 1/2005 | Lee et al. |
| 6,871,114 B1 | 3/2005 | Green et al. |
| 6,927,391 B2 | 8/2005 | Tokuda et al. |
| 6,963,068 B2 | 11/2005 | Asselbergs et al. |
| 6,965,895 B2 | 11/2005 | Smith et al. |
| 6,982,429 B2 | 1/2006 | Robinson et al. |
| 6,993,177 B1 | 1/2006 | Bachelder |
| 7,002,152 B2 | 2/2006 | Grunewald |
| 7,005,636 B2 | 2/2006 | Tappel |
| 7,034,316 B2 | 4/2006 | Wagner et al. |
| 7,041,985 B1 | 5/2006 | Wang et al. |
| 7,045,275 B2 | 5/2006 | Lee et al. |
| 7,047,099 B2 | 5/2006 | Shanmugasundram et al. |
| 7,069,101 B1 | 6/2006 | Arackaparambil et al. |
| 7,095,024 B2 | 8/2006 | Adachi et al. |
| 7,103,439 B1 | 9/2006 | Bode et al. |
| 7,297,965 B2 | 11/2007 | Kidron et al. |
| 7,414,252 B2 | 8/2008 | Moore et al. |
| 7,442,924 B2 | 10/2008 | Giannuzzi et al. |
| 7,511,282 B2 | 3/2009 | Agorio et al. |
| 7,842,920 B2 | 11/2010 | Lundquist |
| 7,880,151 B2 * | 2/2011 | Wells .................. 250/492.1 |
| 2002/0079463 A1 | 6/2002 | Shichi et al. |
| 2006/0011868 A1 | 1/2006 | Kidron et al. |

FOREIGN PATENT DOCUMENTS

| | | |
|---|---|---|
| JP | 11-265679 | 9/1999 |
| WO | 2008051880 | 5/2005 |
| WO | 2008049133 | 4/2008 |
| WO | 2008049134 | 4/2008 |
| WO | 2008051937 | 5/2008 |

OTHER PUBLICATIONS

Giannuzzi, Lucille A., et al., 'FIB Lift-Out Specimen Preparation Techniques,' Introduction to Focused Ion Beams, 2005, Chapter 10.

Langford, Richard M., 'Focused Ion Beams Techniques for Nanomaterials Characterization,' Microscopy Research and Technique, 2006, pp. 538-549, vol. 69.

Lee, Jon C., et al., 'The Versatile Application for In-Situ Lift-Out TEM Sample Preparation by Micromanipulator and Nanomotor,' 2005.

Lensing, Kevin, et al, 'Integrated Metrology and Wafer-Level Control,' Jun. 1, 2006, 6 pgs.

* cited by examiner

METHOD FOR CREATING S/TEM SAMPLE AND SAMPLE STRUCTURE

The present application claims priority from PCT Application No. PCT/US2007/082159, filed Oct. 22, 2007, and from U.S. Prov. Pat. App. No. 60/853,183, filed Oct. 20, 2006, which are hereby incorporated by reference.

TECHNICAL FIELD OF THE INVENTION

The present invention relates to preparation of samples and methods of analysis for transmission electron microscopes and scanning transmission electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM and references to preparing a sample for a TEM are to be understood to also include preparing a sample for viewing on an STEM. The term "S/TEM" as used herein also refers to both TEM and STEM.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the FIB system vacuum chamber are commonly referred to as "in-situ" techniques; sample removal outside the vacuum chamber (as when the entire wafer is transferred to another tool for sample removal) are call "ex-situ" techniques.

Samples which are sufficiently thinned prior to extraction are often transferred to and mounted on a metallic grid covered with a thin electron transparent film for viewing. FIG. 1A shows a sample mounted onto a prior art TEM grid 10. A typical TEM grid 10 is made of copper, nickel, or gold. Although dimensions can vary, a typical grid might have, for example, a diameter of 3.05 mm and have a middle portion 12 consisting of cells 14 of size 90×90 µm² and bars 13 with a width of 35 µm. The electrons in an impinging electron beam will be able to pass through the cells 14, but will be blocked by the bars 13. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. TEM specimens to be analyzed are placed or mounted within cells 14.

For example, in one commonly used ex-situ sample preparation technique, a protective layer 22 of a material such as tungsten is deposited over the area of interest on a sample surface 21 as shown in FIG. 2 using electron beam or ion beam deposition. Next, as shown in FIGS. 3-4, a focused ion beam using a high beam current with a correspondingly large beam size is used to mill large amounts of material away from the front and back portion of the region of interest. The remaining material between the two milled rectangles 24 and 25 forming a thin vertical sample section 20 that includes an area of interest. The trench 25 milled on the back side of the region of interest is smaller than the front trench 24. The smaller back trench is primarily to save time, but the smaller trench also prevents the finished sample from falling over flat into larger milled trenches which may make it difficult to remove the specimen during the micromanipulation operation.

As shown in FIG. 5, once the specimen reaches the desired thickness, the stage is tilted and a U-shaped cut 26 is made at an angle partially along the perimeter of the sample section 20, leaving the sample hanging by tabs 28 at either side at the top of the sample. The small tabs 28 allow the least amount of material to be milled free after the sample is completely FIB polished, reducing the possibility of redeposition artifacts accumulating on the thin specimen. The sample section is then further thinned using progressively finer beam sizes. Finally, the tabs 28 are cut to completely free the thinned lamella 27. Once the final tabs of material are cut free lamella 27 may be observed to move or fall over slightly in the trench. A completed and separated lamella 27 is shown in FIG. 6.

The wafer containing the completed lamella 27 is then removed from the FIB and placed under an optical microscope equipped with a micromanipulator. A probe attached to the micromanipulator is positioned over the lamella and carefully lowered to contact it. Electrostatic forces will attract lamella 27 to the probe tip 29 as shown in FIG. 7. The tip 29 with attached lamella is then typically moved to a TEM grid 10 as shown in FIG. 8 and lowered until lamella is placed on the grid in one of the cells 14 between bars 13.

Whichever method is used, the preparation of sample for TEM analysis is difficult and time consuming. Many of the steps involved in TEM sample preparation and analysis must be performed using instruments operated manually. For this reason, successful TEM sample preparation generally requires the use of highly trained and experienced operators and technicians. Even then, it is very difficult to meet any reasonable standards of reproducibility and throughput.

Use of FIB methods in sample preparation has reduced the time required to prepare samples for TEM analysis down to only a few hours. However, CD metrology often requires multiple samples from different locations on a wafer to sufficiently characterize and qualify a specific process. In some circumstances, for example, it will be desirable to analyze from 15 to 50 TEM samples from a given wafer. When so many samples must be extracted and measured, using known methods the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

Further, existing TEM sample structures are not robust enough to survive automated extraction and mounting. Additionally, TEM structures created using prior art methods often suffer from bending or bowing when thinned to 100 nm or below. In the prior art, manual thinning of TEM sample is halted when bowing observed by the operator. Such manually observation would not be desirable in an automated system.

What is needed is a method to more completely automate the TEM sample extraction and measurement and to increase throughput and reproducibility so that TEM measurement can be incorporated into integrated or in situ metrology for process control. What is also needed is a method of creating a TEM sample that will not suffer from bowing phenomenon when thinned to 100 nm or less and that is robust enough to survive automated extraction and mounting.

SUMMARY OF THE INVENTION

An object of the invention, therefore, is to provide an improved method for TEM sample analysis. Preferred embodiments of the present invention provide improved methods for TEM sample creation, especially for small geometry (<100 nm thick) TEM lamellae. Some preferred embodiments of the present invention provide methods to partially or fully automate TEM sample creation, to make the process of creating and analyzing TEM samples less labor intensive, and to increase throughput and reproducibility of TEM analysis.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Preferred embodiments of the present invention provide improved methods for lamella creation. A preferred embodiment can create S/TEM samples with a thickness in the 50-100 nm range for the purposes of S/TEM metrology with minimal site-to-site variation. The process can produce a 10 μm wide×~5 μm deep×~500 nm thick lamella with a final-thinned window of 3 μm×3 μm at the targeted final thickness (50-100 nm). S/TEM samples produced according to the present invention will not suffer from bowing phenomenon when thinned to 100 nm or less and are robust enough to survive automated extraction and mounting.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Current TEM lamella creation processes for FIB systems use manual input as the primary method for locating a feature or site of interest for lamella creation. Typically, once the desired lamella location is manually located, a fiducial or locating mark is milled nearby. Because FIB imaging necessarily causes some sample damage, a protective layer is deposited over the desired lamella location before imaging and/or milling. The protective layer makes it harder to see features on the substrate so a fiducial mark is typically milled into the protective layer to help orient the beam and locate the proper place for a cut. This fiducial is used in subsequent processing as a locating mark. Image recognition keyed to this fiducial is then used to find the locations for subsequent milling of the lamella. In order to mill the fiducial, a location near the desired lamella site is typically selected manually, and the desired fiducial pattern is then automatically milled at that location.

This method of manually identifying the lamella site and then manually selecting the fiducial location does not provide a high degree of precision or accuracy. As a result, known automatic lamella milling routines are limited to rough milling of lamellae which are approximately 500 nm thick. Further thinning is typically manually controlled in order to achieve the desired lamella thicknesses of 100 nm or less.

Figure 1:
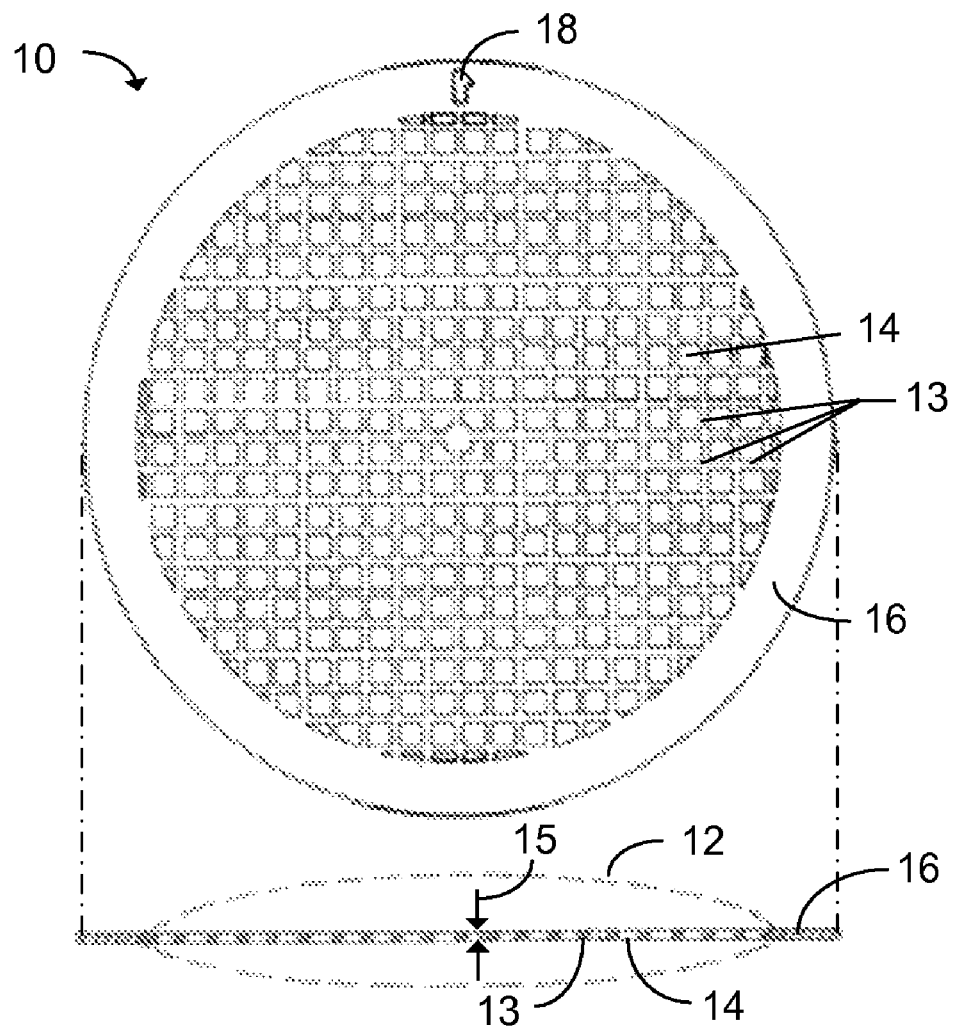
FIG. 1 shows a typical prior art TEM grid.
Figure 2:
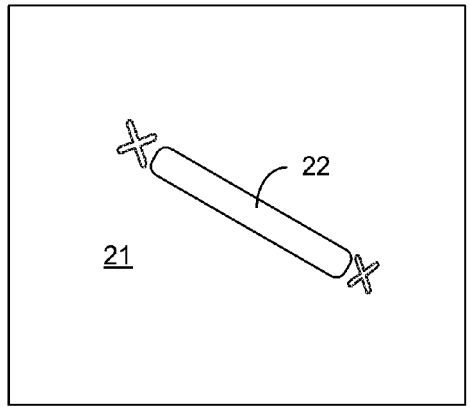
FIGS. 2-5 illustrate the steps in an ex-situ sample preparation technique according to the prior art.
Figure 3:
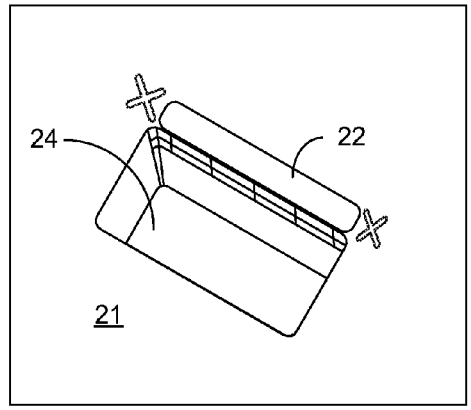
Figure 4:
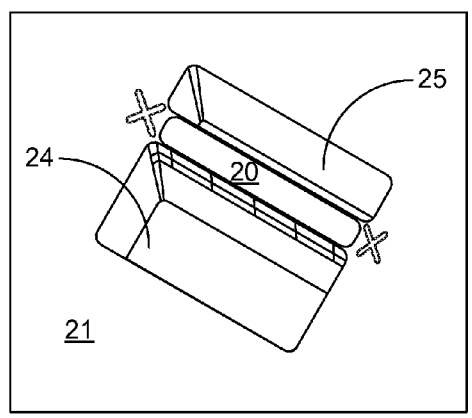
Figure 5:
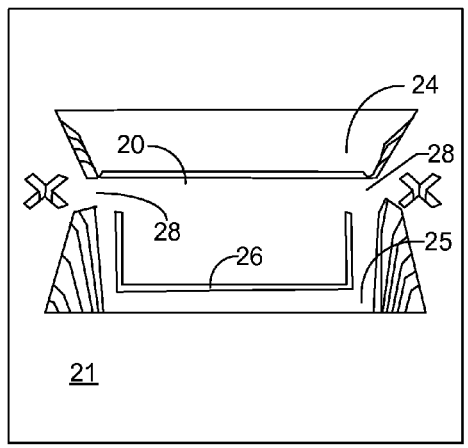
Figure 6:
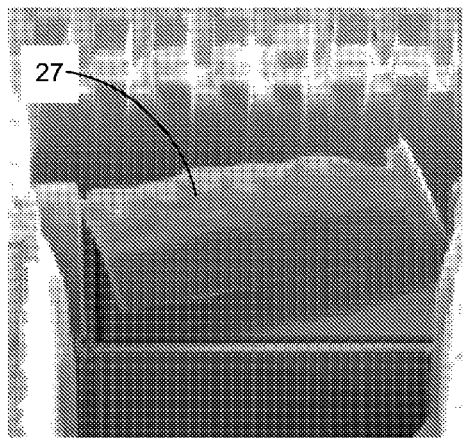
FIG. 6 is a micrograph of a completed and separated lamella according to the prior art.
Figure 7:
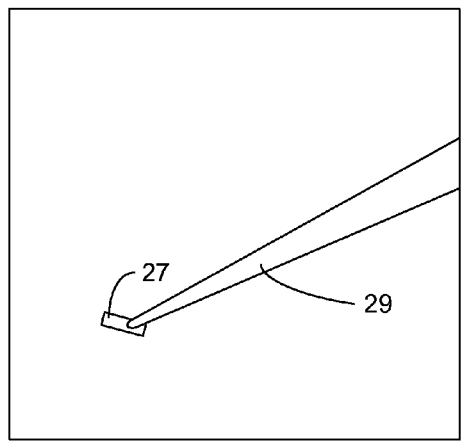
FIGS. 7-8 illustrate the transfer of a lamella using a probe and electrostatic attraction according to the prior art.
Figure 8:
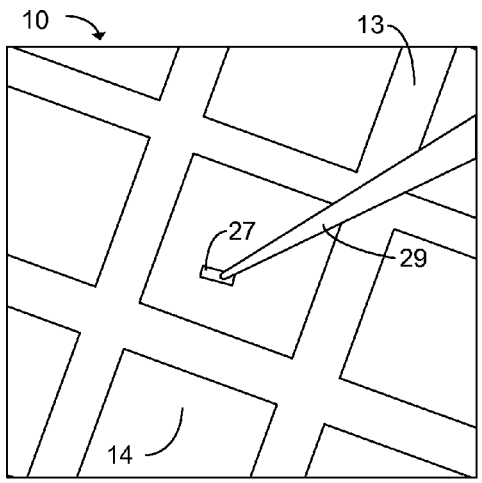
Figure 9:
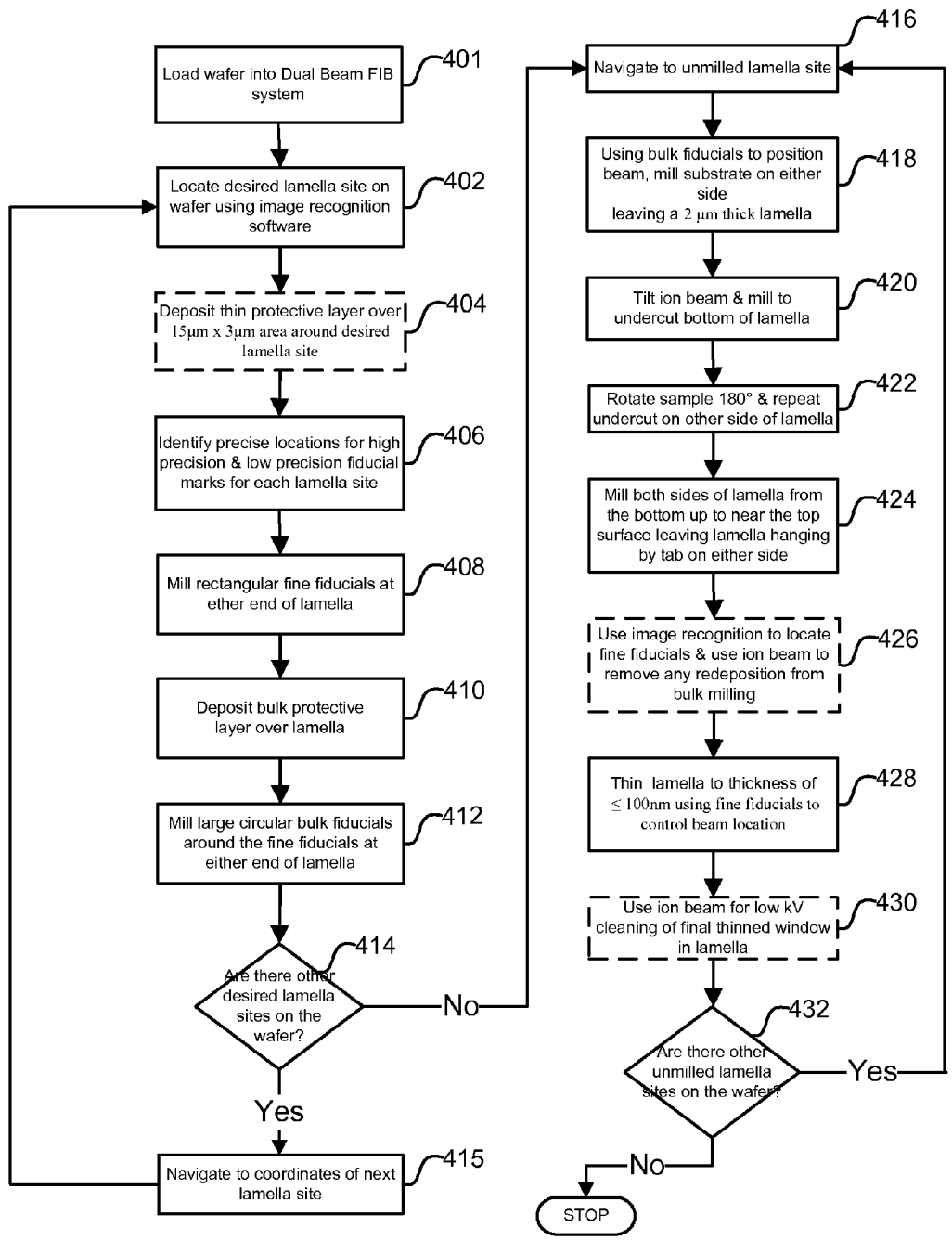
FIG. 9 is a flowchart showing the steps of creating one or more lamellae according to a preferred embodiment of the present invention.

FIG. 9 is a flowchart showing the steps of creating one or more lamellae according to a preferred embodiment of the present invention. In this embodiment, machine-vision based metrology and image recognition, high-precision fiducial marks, and automatic fiducial placement are used to significantly improve lamella placement accuracy and precision. Various steps in the process are shown in FIGS. 10 through 16.

First, in step 401, a wafer is loaded into a FIB system, such as a Certus Dual Beam System, commercially available from FEI Company of Hillsboro, Oreg., the assignee of the present invention. In step 402, lamella sites on the wafer surface are located automatically using image recognition software. Suitable image recognition software is available, for example, from Cognex Corporation of Natick, Mass. Image recognition software can be "trained" to locate the desired lamella locations by using sample images of similar features or by using geometric information from CAD data. Automated FIB or SEM metrology can also be used to identify or help identify the lamella site. Metrology may consist of image-based pattern recognition, edge finding, ADR, center-of-mass calculations, blobs, etc.

In optional step 404, the lamella site is given a protective 5 kV FIB tungsten deposition 15 μm wide by 3 μm tall for 1:20. This provides sufficient tungsten on the site surface to prevent damage during the 30 kV FIB site alignment and deposition steps. This protective layer may be directly placed if the 5 kV 180pA FIB aperture to SEM coincidence is less than 4 μm, otherwise a process of site alignment may be used to refine placement of this deposition.

In step 406, the precise locations of any desired fiducial marks with respect to each desired lamella location are specified. For example, using a FIB or SEM to image a sample location, a fiducial location could be specified by an operator using a mouse to drag a virtual box around the desired fiducial location. Automated metrology software could then precisely measure the location of the fiducial with respect to identifiable features at the sample location (for example 15 nm from the right edge of the feature). When each lamella site is located, a fiducial can then be automatically milled at each lamella site at the precise location specified so that the spatial relationship between each fiducial and each lamella location will be identical. A fiducial location could also be specified using CAD data to specify the location of the fiducial with respect to a particular structure on the wafer surface.

In a preferred embodiment, precise fiducial placement is accomplished through the use of the IC3D™ software's vision tools. A specified pattern can be located by image recognition software and used to locate a target structure. A series of calipers—a pattern recognition tool that locates edges—are then used to find the edges of the target structure and to precisely center the fine fiducials around the target structure. Extensive use of IC3D's shape linking capabilities allows robust placement of site fiducials based on direct measurement of each site.

Preferably, a combination of high precision (fine) fiducials and low precision (bulk) fiducials are used to optimize lamella placement precision and accuracy. Currently, fiducials used for lamella location and milling consist only of low-precision features such as an "X" formed by the intersection of two milled lines. At the resolutions necessary for adequate lamella production, however, each milled line will be several nanometers wide. Edge detection software must be used to determine the centerline of each milled line and then the intersection of the two mathematically determined centerlines used to determine a particular reference point. There is typically too much error in this type of determination to use the fiducial to accurately determine a lamella location within the margin of error needed for many small-geometry lamella applications.

Figure 10:
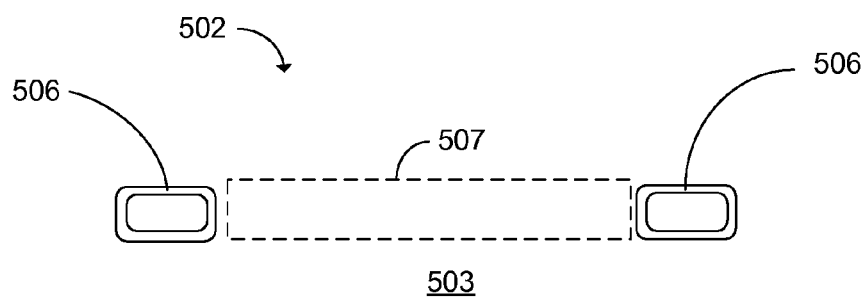
FIG. 10 shows a lamella site according to the process of FIG. 11 after high precision fiducials have been milled and a protective layer deposited over the lamella location.

In a preferred embodiment, a combination of typical low-precision fiducial marks and higher precision marks are used. High-precision fiducials, such as the rectangles 506 shown in FIG. 10 allow the lamella location to be much more accurately determined. The rectangular fiducials 506 shown in FIG. 10 are located at either end of the desired lamella location. High-precision fiducial are smaller than the low-precision fiducials discussed below. For this reason, the high-precision fiducials are not identifiable with the large FIB beams used for bulk milling, and are only used for final placement of the lamella with smaller FIB beams. The rectangular fiducials in FIG. 10 are located using image analysis to determine the Y position of their top and bottom edges. This results accurate positioning even when the fiducial is damaged during FIB imaging. Edge detection software only has to identify the top and bottom edges to precisely locate the top and bottom edges of the lamella. Pattern recognition for these rectangular fiducials is based on a two-measurement strategy—the top and bottom edges of the fiducial are measured. Once the edge positions are located, a central line or axis can be determined which is parallel to the top and bottom edges of the lamella. As the sample is imaged with the FIB, the top surface is progressively sputtered away. The high precision fiducial described above is very tolerant of this FIB damage because both measured edges will be altered at nearly the same rate, so the overall error in lamella placement will be very low.

Figure 11:
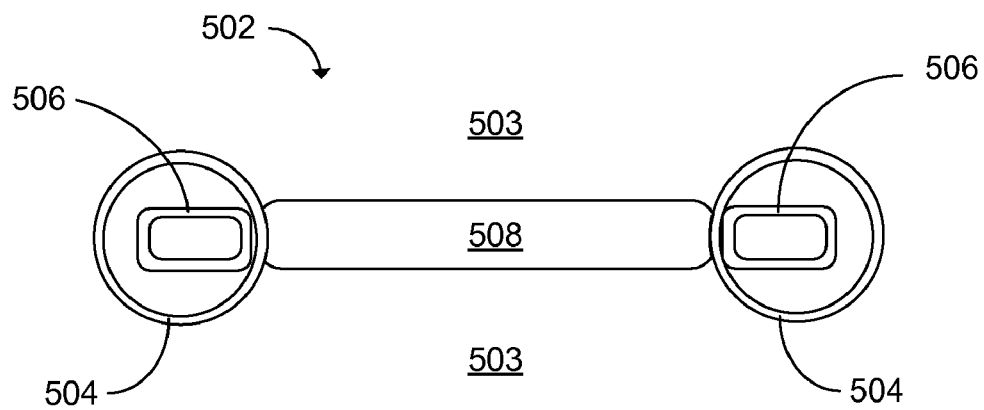
FIG. 11 shows a lamella site according to the process of FIG. 11 after low precision fiducials have been milled.

Low-precision fiducials, such as the large circles 504 in FIG. 11, can be used for gross-structure pattern recognition, such as quickly finding the approximate lamella location and performing the bulk milling. Suitable low-precision fiducials can be easily identified when the sample is imaged with a low resolution (higher beam size) ion beam suitable for rapid bulk material removal. Multiple fiducials and combinations of low and high precision fiducials and different fiducial shapes (as shown in FIG. 11) can be used for even more accurate orientation.

Once the fiducial locations have been determined, in step 408, high precision fiducials are milled at the desired locations. As shown in FIG. 10, a small rectangular feature 506 is milled at each end of the lamella site (which is indicated by dashed line 507) with the 1 nA 30 kV FIB for vertical placement of the lamella during the final thinning process. In a preferred embodiment, a suitable fiducial pattern will allow the final lamella placement to be accurate within 10 nm. In some embodiments, the size and shape of the fiducial can be varied depending on the size, width, or location of the desired lamella.

In step 410, after the high precision fiducials have been milled, a bulk protective layer 508 composed of, for example, tungsten or platinum is deposited over the lamella site to protect the sample from damage during the milling process. FIG. 11 shows a lamella site 502 with a protective layer 508 deposited over the desired lamella location on a wafer surface 503. For some samples where information is required very close to the surface, it may be useful to deposit the protective layer using a low energy FIB (~5 keV) to perform the deposition. The high precision fiducials 506 are also preferably lightly backfilled with the protective material to protect them during future processing.

In step 412, after the bulk protective deposition, large circular fiducials 504 as shown in FIG. 11 are milled around the fine fiducials. These low-precision fiducials are used for gross-structure pattern recognition, such as quickly re-finding the approximate lamella location and determining the location for bulk milling of the lamella. Because a larger beam size will be used for the bulk milling, a suitable low precision fiducial should be easily identified by pattern recognition software even in lower resolution images. The system can then readily relocate each desired lamella site by locating the fiducial and knowing that the lamella site is positioned at a fixed offset from the fiducial.

Figure 12:
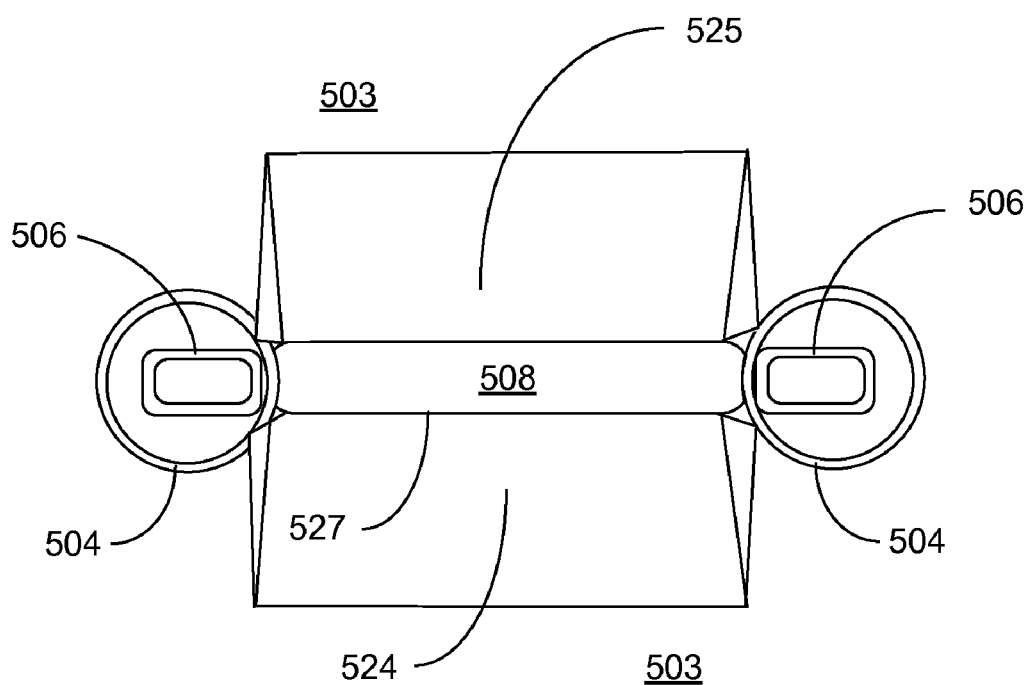
FIG. 12 shows a lamella site according to the process of FIG. 11 after bulk milling has been completed.

If there are other lamella sites on the wafer, step 414, the FIB system navigates to the coordinates of the next lamella site in step 415. The process then returns to step 402 and steps 402 to 414 are repeated for all remaining lamella sites before the lamella milling process is started. Once fiducials have been milled at all lamella sites, in step 416, the FIB system navigates to an unmilled lamella site. In step 418, bulk substrate milling is used to roughly shape the lamella. FIG. 12 shows a lamella site after the bulk milling of step 418 has been completed. A larger ion beam size will be suitable for bulk material removal. In a preferred embodiment, each lamella will be formed by using a FIB to cut two adjacent rectangles 524, 525 on a substrate, the remaining material between the two rectangles forming a thin vertical sample section 527 that includes an area of interest. Preferably, an ion beam will be directed at the substrate at a substantially normal angle with respect to the substrate surface. The beam will be scanned in a rectangular area adjacent to the sample section to be extracted, thus forming a rectangular hole 524 having a predetermined depth. The milled hole should be sufficiently deep to include the feature of interest in the extracted sample. Preferably, the milled hole is also deep enough to allow for bulk material to remain at the bottom of the thinned sample (beneath the feature of interest) to increase the mechanical rigidity of the sample as discussed below. The beam will be scanned in a rectangular area 525 adjacent to the sample section to be extracted, but on the opposite side of said sample section from the first rectangular hole. The remaining material between the two rectangular holes will preferably form a thin vertical sample section that includes the lamella to be extracted.

Figure 13:
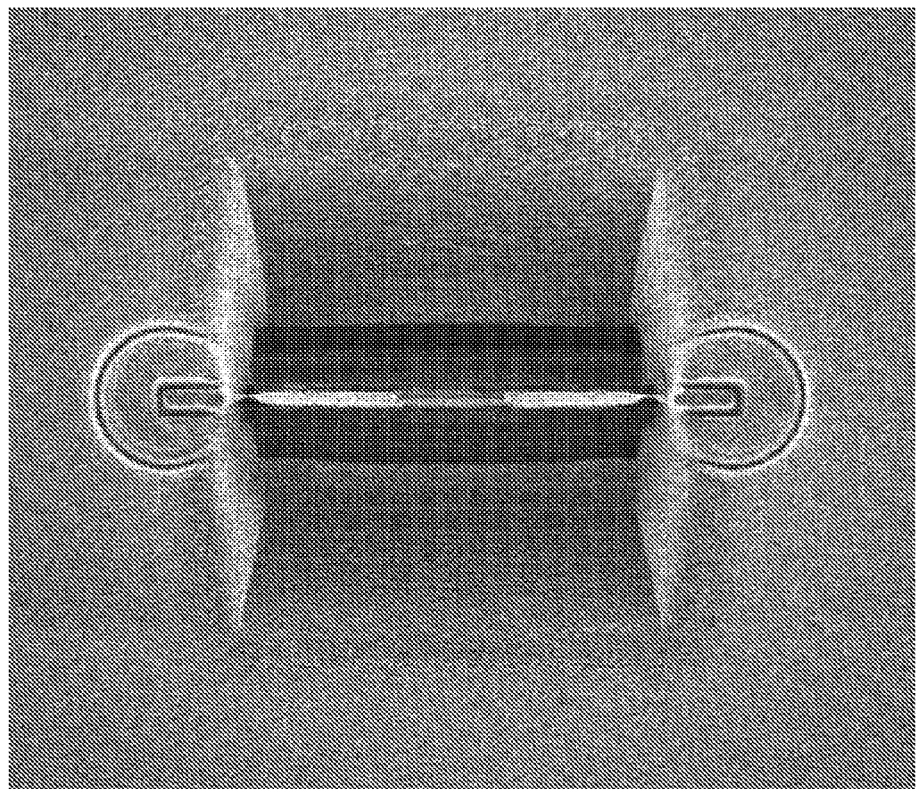
FIG. 13 shows a high resolution micrograph of a lamella sample according to the present invention after bulk milling has been completed.

Low-precision fiducials 504 can be used to control the beam location for bulk milling of the lamella (using a larger beam diameter for more rapid sample removal). A typical cross-section mill pattern can be used coming in from both sides of the lamella, leaving a coarse lamella approximately 2 μm thick. The lamella is then further thinned to approximately 800 nm with a cleaning cross-section mill on both sides in preparation for the undercut step. FIG. 13 shows a high resolution micrograph of a lamella sample after bulk milling has been completed.

Figure 14:
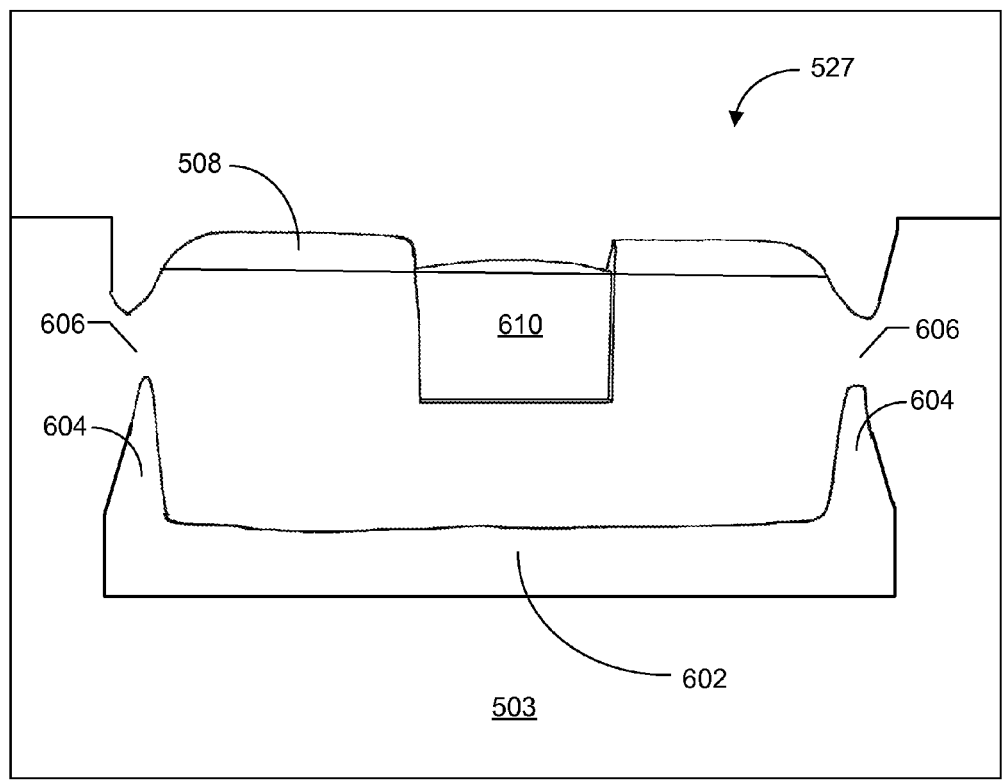
FIG. 14 shows a lamella created according to the process of FIG. 11.

In step 420, after the fiducials and bulk mills are done, the lamella undergoes an undercutting process. The FIB column is preferably tilted to approximately 4.5 degrees and the lamella bottom undercut with a cleaning cross-section at 1 nA. Alternatively, the sample stage could be tilted. The precise location for the undercut can be located using vision tools to locate and measure the fine fiducials. Although a greater FIB tilt could be employed (subject to hardware constraints) a shallow incidence angle undercutting provides two benefits to the TEM sample preparation process. First, the lamella face is not imaged at a high incidence angle, thus reducing Ga+ implantation and damage; and second, the undercutting process serves as an intermediate thinning step that has been shown to reduce the lamella thickness to a reasonably narrow range of widths for a number of different substrates (TI SiGe, TI STI, MetroCal, IFX DTMO, Fujitsu contact). The undercut 602 and side cuts 604 for a lamella sample 527 are shown in FIG. 14.

In step 422, the sample is then rotated 180 degrees and the process repeated on the top edge of the lamella in order to cut the bottom free. This results in a rough lamella that is roughly 500 nm thick centered around the target structure.

In step 424, two cuts are made from the bottom of the lamella up to near the top surface in order to cut the sides of the lamella free, but leaving the lamella hanging by a tab 606 (shown in FIG. 14) on either side at the top of lamella. Once the final thinning of the lamella has been completed, a probe can be attached to the lamella and the tabs or hinges severed so that the lamella can be extracted. Alternatively, a probe can be used to break the lamella hinges as described in co-pending PCT App. No. PCT/US07/82030, filed on Oct. 20, 2007, which is hereby incorporated by reference.

In optional step 426, IC3D vision tools can be used to locate the fine fiducials and remove any redeposition from the bulk milling process as well as the protective tungsten layer deposited during the fiducial milling process.

The lamella formed by the first two rectangular bulk-milling cuts and the undercutting will preferably be roughly 500 nm thick. In step 428, the center of the lamella (containing the area of interest) is thinned from both sides, preferably using a 30 pA beam at 1.2 degrees of FIB tilt with the mill pattern described below. As discussed below, the typical cleaning mill pattern commonly used for lamella milling causes very thin lamellae (<100 nm) to bend or bow. Applicants have discovered that using a mill pattern resulting in multiple passes of the beam on the sample face prevents the sample from bowing. This mill pattern, along with other embodiments of a method for eliminating lamella bowing during the thinning process, is discussed in greater detail below.

The final thinning cuts can be placed using calipers (with image recognition) to find the lamella edges, with the final lamella thickness being determined by an offset in the milling position from the lamella face. For example, for each lamella to be extracted from a sample, the exact location of the lamella can be determined from the fiducial location. The first cut is milled at half the desired lamella thickness away from the center of the desired sample. Viewing the sample from the top down, using either FIB or SEM imaging, automated metrology software can then measure the edge of the first cut and the fiducial location and precisely determine the location of the second cut. Using the location of the high precision fiducials to precisely control beam location, the lamella can then be thinned using a finely focused FIB to a thickness of 100 nm or less in a process that is also highly repeatable.

Preferably, real time pattern recognition can be used to position the FIB. A suitable FIB system providing real time pattern recognition and metrology is the Certus 3D Dual Beam System available from FEI Company, the assignee of the present invention.

In optional step 430, low-kV cleaning is performed on the final thinned window with a 180 pA 5 kV FIB at 4.5 degrees of tilt. Applicants have discovered that a 10 second cleaning mill on each face of the lamella produces a significant improvement in TEM imaging conditions.

If there are other unmilled lamella sites on the wafer, in step 432, the FIB system navigates to the coordinates of the next unmilled lamella site. The process then returns to step 416 and steps 416 to 432 are repeated for all remaining unmilled lamella sites.

Figure 15:
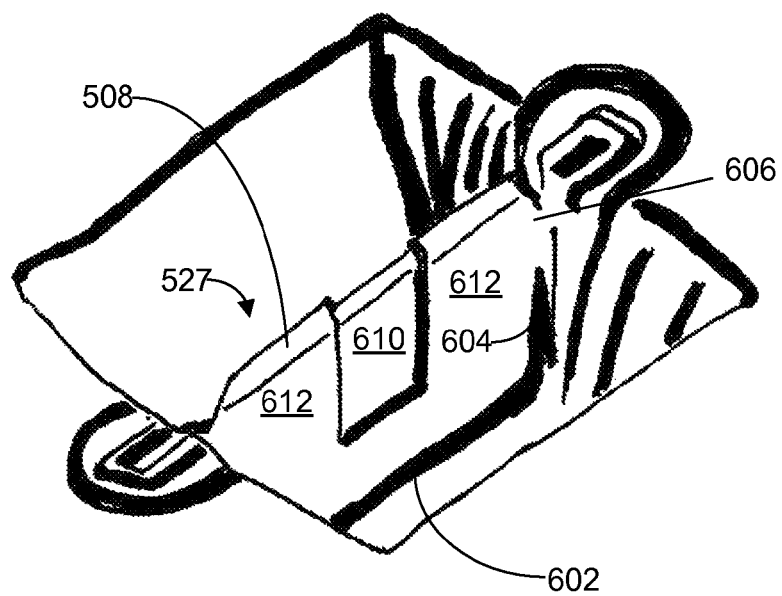
FIG. 15 shows a lamella created according to the process of FIG. 11.
Figure 16:
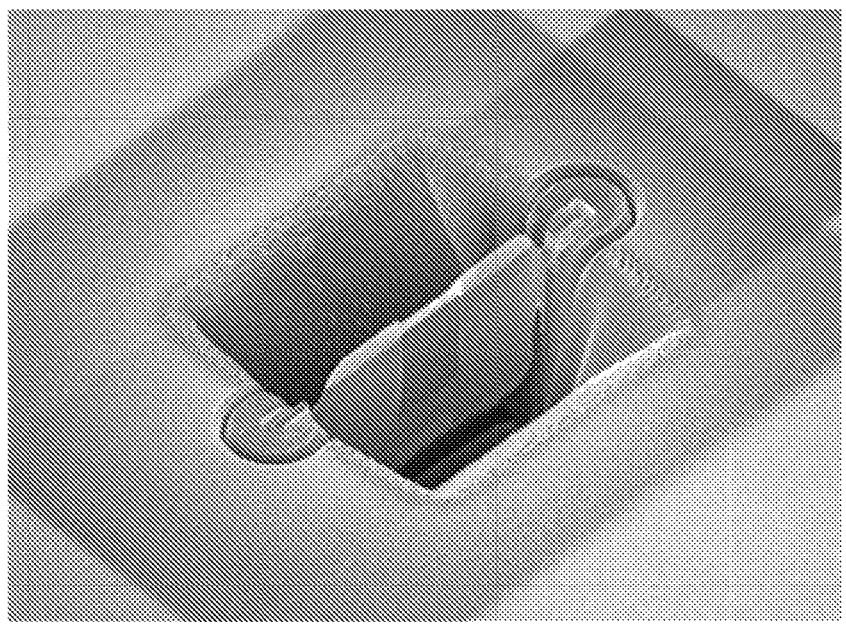
FIG. 16 shows a high resolution micrograph of a lamella according to the present invention.

The final lamella structure produced by the method of discussed in reference to FIG. 9 is shown in FIGS. 14-16. As discussed below, a center lamella "window" 610 can be thinned to a thickness of 100 nm or less, leaving thicker surrounding material to provide the sample with increased mechanical strength. Preferably, the center window is approximately 3 μm wide, 4 μm deep, and 50-70 nm thick. The thicker material surrounding window 610, indicated by reference numeral 612 in FIG. 15, also helps prevent the lamella from bowing during the milling process. The increased mechanical strength of this "windowed" lamella structure is also very desirable when using an ex-situ lamella extraction device as described in co-pending PCT App. No. PCT/US07/82030, filed on Oct. 20, 2007, which is incorporated by reference. FIG. 16 shows a high resolution micrograph of a lamella created using the process described above.

Figure 17A:
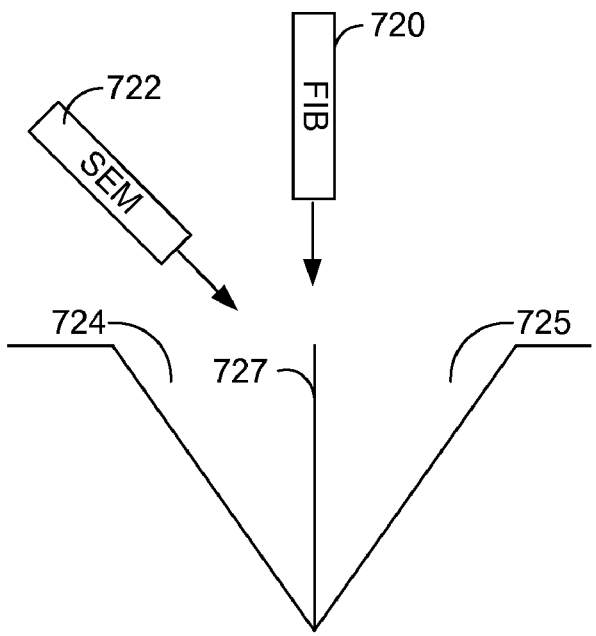
FIG. 17A shows a graphical representation of a dual beam system where one beam is used to thin the lamella while the other beam images the lamella to endpoint milling.
Figure 17B:
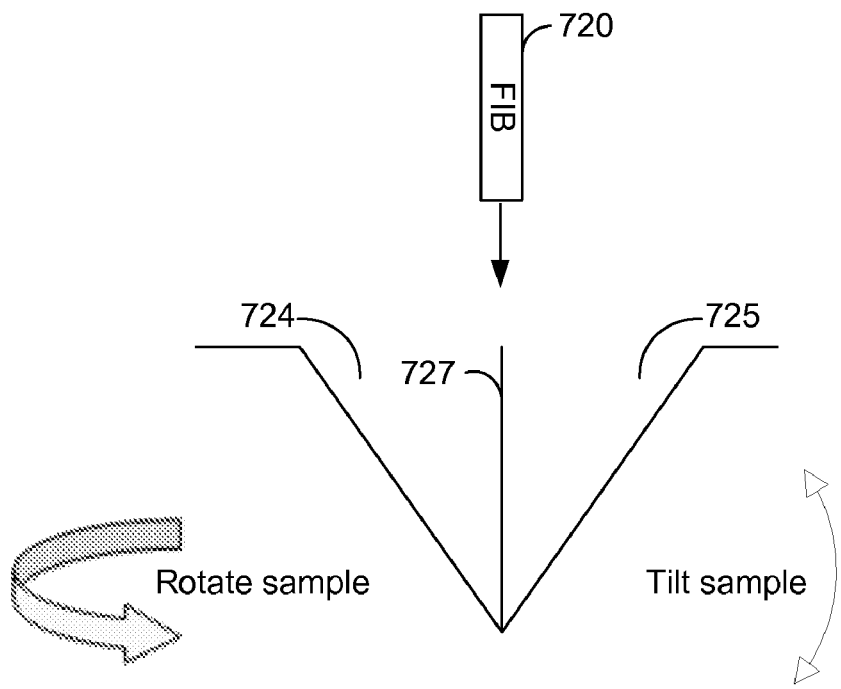
FIG. 17B shows a graphical representation of a single beam system where the sample must be rotated to allow one beam to mill and image for endpointing.

In addition to determining mill locations relative to fiducial marks as discussed above, the milling process can be end-pointed using top down pattern recognition and metrology. In a preferred embodiment, FIB milling is carried out in a dual beam FIB/SEM system, as shown schematically in FIG. 17A (not to scale) with vertically mounted FIB column 720 used to mill substrate 503 to create lamella 727 and the SEM column 722 used to image the lamella 727 so that automated metrology software can determine whether the lamella has been thinned to the desired thickness. Alternatively, a dual FIB system could be used with one beam used to mill and the other used to image. As shown schematically in FIG. 17B (not to scale), a system with a single FIB column 720 could also be used and the sample tilted and rotated so that the same beam could be used to mill and image (as is known in the prior art). Skilled persons will recognize that there is a danger of damage to the lamella if a FIB is used to image the sample.

Figure 17C:
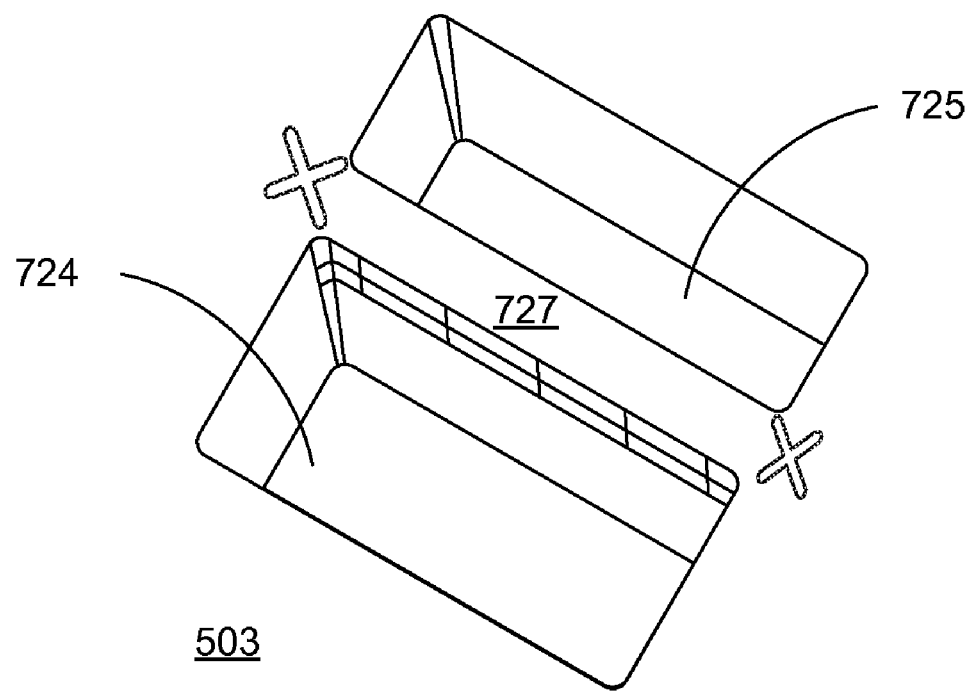
FIG. 17C shows a lamella site during the milling process which could be imaged and the image processed according to the present invention to endpoint milling.
Figure 18:
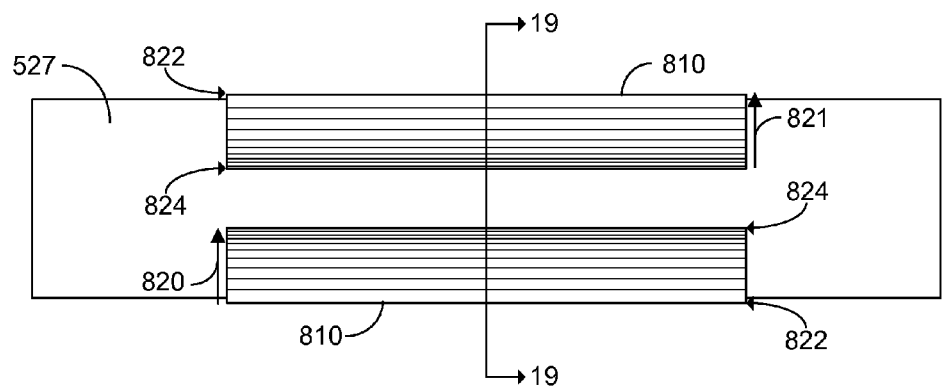
FIG. 18 show a graphical illustration of a milling pattern according to the present invention that is used to thin the TEM sample

Referring also to FIG. 17C, after the initial bulk mill 724 is completed on one side of the lamella 727, the endpoint of the second bulk mill 725 can be controlled by monitoring the width of the lamella in the same fashion that cross-sections for sub-100 nm features are measured by a CD-SEM.

Typically, to measure the width of cross-section of a structure, a SEM is used in conjunction with automatic metrology software. As the electron beam is scanned across the exposed cross-section, whether secondary or backscattered detection is employed, there will typically be a change in electron intensity at the edges of the structure. An algorithm is used to assign an edge position based upon the contrast at the edges of the structure and to determine the distance between those edges.

A preferred embodiment of the present invention makes a novel application of these known techniques for cross-section metrology. The final lamella position and thickness would be based on a mill and image technique similar to known slice and view techniques where the FIB in a dual beam system is used to expose a sample cross section and the SEM is used to image the sample for automated metrology analysis. Image processing tools such as pattern recognition and edge finding tools can thus be used to precisely control lamella thickness. These types of prior art "slice and view" techniques are described, for example, in U.S. patent application Ser. No. 11/252,115 by Chitturi et al. for "Method Of Measuring Three-Dimensional Surface Roughness Of A Structure," which is hereby incorporated by reference, and which is assigned to FEI Company, the assignee of the present invention.

Preferably, thinning would first be completed on one side of the lamella. The location of the initial milling would be controlled using fiducial location or other metrology as discussed above. The sample would then be imaged from the top down with either a focused ion beam or scanning electron microscope. As with a CD-SEM, when either the ion beam or the electron beam strikes the surface of substrate, secondary electrons and backscattered electrons are emitted. Respectively, these electrons will be detected by a secondary electron detector or backscattered electron detector as is known in the art. The analog signal produced either by secondary electron detector or backscattered electron detector is converted into a digital brightness values. As the beam (either ion or electron) is scanned across the lamella surface, there will be a change in emitted electron intensity at the edges of the structure. An algorithm is used to assign an edge position based upon the difference in brightness values or contrast at either of the edges of the structure and to determine the distance between those edges. If analysis of the image determines that certain specified criteria are not met (such as, for example, a minimum desired lamella/sample width) then the mill and image processing steps are repeated.

Automated cross-section metrology using CD-SEM has long been used to determine critical dimensions at the sub-100 nm level. As a result, the processes involved have been refined to levels of reliability far beyond those seen with other less common techniques. CD-SEM metrology techniques can thus provide levels of reliability and repeatability that are sufficient to allow the use of TEM samples for in-line process control. This type of automated process control has not been practical in the prior art because of the problems with sample bowing discussed above. However, by using the combination of the milling algorithm and sample structure described herein, sample bowing at or below 100 nm can be greatly minimized. This allows the use of automation of the end-pointing process and eliminates the time consuming manual thinning of the prior art, thus enabling higher volume automated lamella creation for specific structures.

A suitable dual beam FIB/SEM for practicing a preferred embodiment of the present invention would be the CLM-3D Dual Beam System available from FEI Company, the assignee of the present invention. Suitable software to implement fully or partially automated image processing, metrology, and machine control according to the present invention should provide pattern recognition and edge detection tools, along with "do while" looping capabilities, such as the IC3D™ software also available from FEI Company.

As discussed above, the bending or bowing commonly associated with thin (less than 100 nm thick) TEM samples can be minimized by using a novel milling pattern to thin the center window of the lamella. Final thinning of lamellae according to the prior art typically makes use of a milling pattern, often referred to as a clean up cut or cleaning cross section, where the ion beam is scanned one line at a time toward a feature of interest. With this cutting pattern, the beam executes a set of line cuts in serial mode. The idea is to gradually step the line cuts into the exposed surface to clean it. All lines are milled consecutively; milling is completed for each line before moving to the next. The beam is then stepped (in the y-direction) toward the desired sample face and the process is repeated. Milling is completed in one pass, largely to prevent redeposition of sputtered material on the lamella sample face.

Although the pattern may be varied slightly, the beam is essentially in contact with the cut face almost continuously. Although the exact mechanism is unclear, the end result is that the sample will begin to bow or warp away from the beam when the sample gets thinner than about 70 nm. Sample warping is a significant problem because accurate metrology on a warped sample is very difficult. Further, the region of interest can be damaged so that it becomes unusable for further analysis.

Referring to FIGS. 18 and 19A through 19C, in a preferred embodiment of the present invention, the TEM sample 527 is thinned by using a FIB milling pattern that repeatedly steps into the sample cut face in the y-direction (as shown by arrow 820) with a decreasing scan speed in (and thus a longer/increasing dwell time as the beam steps into the sample). By "decreasing scan speed," Applicants mean that the time between steps becomes longer as the beam approaches the desired sample face (although the speed at which the beam is scanned back and forth in the x-direction may not change). Further, several passes of the beam are used to reach the desired mill depth for the sample face. Mill boxes 810 are not intended to show the exact number of steps or the distance between steps, but rather the line gradient is intended to illustrate the decreasing scan speed and the increasing dwell time as the beam moves toward the final sample face. Although similar raster patterns are known in the prior art, they have typically been used to rapidly mill deep holes in a substrate. Applicants have discovered, however, that this pattern can be used to precisely thin a lamella without causing sample bowing. This type of raster pattern is typically not used for precise milling of very small structures, primarily because of concerns over redeposition of sputtered material. When used to mill deep holes, the process is often stopped to evaluate the milling progress. By using the pattern on an automated tool and letting the milling finish without stopping, redeposition is greatly minimized.

Figure 19A:
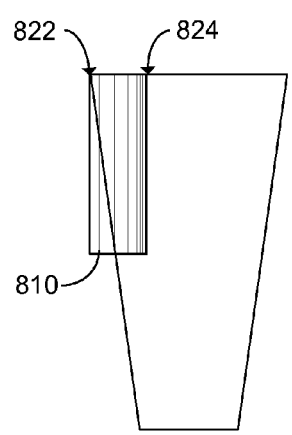
FIGS. 19A through 19C show steps in the milling process of FIG. 18 on a cross section view of a TEM sample.
Figure 19B:
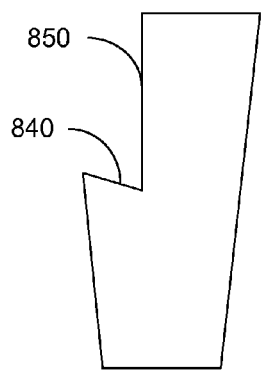
Figure 19C:
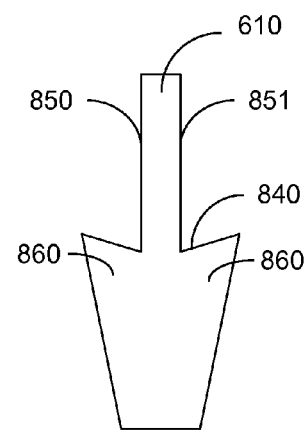

By decreasing the scan speed (and thus increasing the dwell time) of the ion beam as the beam moves in the y-direction as shown by arrow 820, the total beam current is increased for each x-location at each successive beam step as the beam moves toward the desired sample face 850, 851. This allows for differential milling of the sample, with deeper milling occurring at the sample face 850. FIGS. 19A to 19C shows a cross-section of the sample 527 taken along line 19 in FIG. 18 at various times during the milling process. As shown in FIG. 19B, the depth of the milled trench 840 slopes toward the sample face 850 (getting deeper as the sample face is approached). Milling throughput is thus increased (because areas away from the sample face do not need to be milled as deeply). The preservation of sample bulk material 860 at the bottom of the lamella window 610 also increases the mechanical rigidity of the sample and improves its handling characteristics.

In addition to the varying dwell time or step size, several passes of the ion beam are preferably used to reach the desired mill depth for the sample face. Preferably, these multiple beam passes are made without changing the beam angle, energy, current, current density, or diameter. In contrast to the clean up cut described above, the ion beam is not kept in constant contact with the sample face. For example, five or six passes could be used to mill final TEM sample 527. Each pass only mills a fraction of the desired depth from initial y-coordinate 822 to final y-coordinate 824. If the desired sample face depth has not been achieved when a pass is completed, the beam is moved away from the sample face (in the y-direction as shown by arrow 821) back to initial y-coordinate 822 to begin another pass. Applicants now believe that sample bowing in the prior art results from either electrostatic forces or thermal buildup as the beam is in contact with the sample face. By using multiple passes so that the beam is not in constant contact with the sample face, any heat/electrostatic charge buildup is allowed to dissipate between ion beam passes. As a result, bowing of the final TEM sample 527 is largely eliminated, even for samples as thin as 50 nm.

In many embodiments, all cuts can be performed using a single beam current, for example, a 20 nA beam current using beam energies that are readily available with many commercial FIB instruments (e.g., 10 s of keV), with a dwell time and step size that is typically used for FIB milling of Si. While preferred process parameters are described, skilled persons will understand that the preferred process parameters will vary with the size and shape of the sample and the material of the substrate. Skilled persons will be able to readily determine suitable process parameters for extracting samples in different applications.

Figure 20:
FIG. 20 is a high resolution micrograph of a lamella sample with a thinner central "window" prepared according to the present invention.

As shown in FIGS. 14-16, the process described above can be used to further thin a center lamella "window" 610 to a thickness of 100 nm or less, preferably using the milling pattern discussed above, leaving thicker surrounding material to provide the sample with increased mechanical strength. Preferably, the center window is approximately 3 µm wide, 4 µm deep, and 50-70 nm thick. The thicker material surrounding window 610, indicated by reference numeral 612 in FIG. 15, also helps prevent the lamella from bowing during the milling process. The increased mechanical strength of this "windowed" lamella structure is also very desirable when using an ex-situ lamella extraction device as described in co-pending PCT App. No. PCT/US07/82030, filed on Oct. 20, 2007, which is incorporated by reference. FIG. 20 is a high resolution micrograph of a lamella sample with a thinner central "window" prepared according to the present invention using the mill pattern described above.

Alternatively, in some circumstances it might be desirable to use the mill pattern described above to thin the entire lamella to a uniform thickness of 100 nm or less (without a thinner central "window"). Although such a structure would not have the increased mechanical strength of a windowed structure (due to the thicker material at the sides and bottom) sample bowing would still be significantly reduced over the prior art.

The present invention provides a number of significant advantages over the prior art. Using typical methods for TEM sample preparation, it takes highly trained and experienced operators approximately 3 hours to create and extract one sample lamella suitable for TEM analysis. For current in-line metrology techniques like top-down SEM or CD-SEM analysis, as many as 20 different sites across a wafer might be need to be measured. Using prior art methods of TEM sample preparation, it would take about 60 hours just to prepare suitable TEM samples from 20 different sites.

Also, because so much of the TEM sample preparation must be performed manually, the process is very labor intensive and requires the use of highly skilled operators (which of course translates into high labor costs).

Further, current manual TEM sample preparation methods produce samples having a great deal of variation. In order to use a metrology technique for process control, it is highly desirable that the samples be as uniform as possible. Because current methods require the final thinning of a TEM lamella to be manually controlled, there is an unavoidable variation in sample thickness for lamellae from different sample sites. Manual control over other key elements in the sample creation process, such as fiducial placement (which determines the actual lamella location) introduces even more variation and further reduces the precision of the final lamella preparation. The variation between samples is even greater when lamellae are prepared by different operators.

Using the present invention, however, results in a significant improvement in the TEM sample preparation process. As discussed above, preferred embodiments of the present invention have been used to create and extract S/TEM samples with a thickness in the 50-100 nm range with very minimal site-to-site variation. The process produces a lamella in roughly 18 minutes, with a site-to-site 3-sigma final lamella thickness variation of roughly 20 nm. The time required to sample 20 different sites on a wafer surface drops to about 6 hours (as opposed to 60 hours for current methods). The process is also much less labor intensive and does not require operators with as high a degree of training or experience. Because more of the process is automated, variation between lamella samples is also minimized.

The increased throughput and reproducibility of the TEM analysis provided by the present invention will allow TEM based metrology on objects such as integrated circuits on semiconductor wafer to be used for in-line process control. For example, TEM analysis according to the present invention could be utilized in a wafer fabrication facility to provide rapid feedback to process engineers to troubleshoot or improve processes. This kind of process control for the very small features that can only be measured by TEM is not possible using prior art TEM sample preparation methods.

The invention has broad applicability and can provide many benefits as described and shown in the examples above. The embodiments will vary greatly depending upon the specific application, and not every embodiment will provide all of the benefits and meet all of the objectives that are achievable by the invention. For example, in a preferred embodiment TEM lamella samples are created using a gallium liquid metal ion source to produce a beam of gallium ions focused to a sub-micrometer spot. Such focused ion beam systems are commercially available, for example, from FEI Company, the assignee of the present application. However, even though much of the previous description is directed toward the use of FIB milling, the milling beam used to process the desired TEM samples could comprise, for example, an electron beam, a laser beam, or a focused or shaped ion beam, for example, from a liquid metal ion source or a plasma ion source, or any other charged particle beam.

Also, the invention described above could be used with automatic defect reviewing (ADR) techniques, which could identify defects via die-to-die or cell-to-cell ADR. A lamella containing the defect could be created and removed with or without milling fiducials. Although much of the previous description is directed at semiconductor wafers, the invention could be applied to any suitable substrate or surface. Further, whenever the terms "automatic" "automated" or similar terms are used herein, those terms will be understood to include manual initiation of the automatic or automated process or step. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. An method of extracting one or more samples for TEM analysis from a substrate, the method comprising:
    loading the substrate with the sample to be extracted into an ion beam system;
    locating a first sample site on the substrate surface;
    imaging the sample site;
    identifying at least one desired first fiducial location for said first sample site;
    milling a combination of at least one high precision fiducial mark and one low precision fiducial mark at the desired first fiducial locations;
    determining the edge positions for the desired sample with respect to said fiducial marks;
    automatically milling the substrate surface on either side of the desired sample location leaving a thin layer of material; and
    extracting the sample.

2. The method of claim 1 where the substrate comprises a semiconductor wafer.

3. The method of claim 1 wherein automatically milling the substrate surface on either side of the desired sample location leaving a thin layer of material comprises automatically milling the substrate surface on either side of the desired sample location leaving a thin layer of material less than 500 nm thick.

4. The method of claim 1 wherein automatically milling the substrate surface on either side of the desired sample location leaving a thin layer of material comprises automatically milling the substrate surface on either side of the desired sample location leaving a thin layer of material less than 100 nm thick.

5. The method of claim 1 in which locating the sample site on the substrate surface comprises locating the sample site on the substrate surface using image recognition software.

6. The method of claim 1 in which identifying at least one desired first fiducial location for said first sample site comprises manually locating at least one desired first fiducial location for said first sample site.

7. The method of claim 1 further comprising:
    locating a second sample site on the substrate surface;
    using pattern recognition to identify at least one second fiducial location for said second sample site so that the spatial relationships between said second fiducial location and said second sample site will be identical to the spatial relationships between said first fiducial location and said first sample site.

8. The method of claim 1 in which identifying at least one desired first fiducial location for said first sample site comprises locating said first fiducial location from CAD data and locating the desired fiducial location on the substrate by using pattern recognition based upon geometric information from the CAD data.

9. The method of claim 1 in which milling a combination of at least one high precision fiducial mark and one low precision fiducial mark comprises milling at least one larger fiducial mark which is recognizable in an image of the sample produced by an ion beam scan at a lower resolution suitable for bulk milling and at least one smaller fiducial mark which is recognizable in an image of the sample produced by an ion beam scan at a higher resolution.

10. The method of claim 1 in which automatically milling the substrate surface on either side of the desired sample location leaving a thin layer of material comprises:
    imaging the desired sample location and the at least one low precision fiducial using an ion beam having a first large beam diameter suitable for bulk milling;
    positioning the ion beam using the location of the at least one low precision fiducial;
    scanning the beam in a rectangular area on a first side of the desired sample location to form a first rectangular hole having a predetermined depth; and
    scanning the beam in a rectangular area on a second side, said second side on the opposite side of the desired sample location from the first side, to form a second rectangular hole having a predetermined depth leaving a vertical layer of material between said first and second rectangular holes, said layer including the sample section to be extracted.

11. The method of claim 10 further comprising:
    imaging the desired sample location and the at least one high precision fiducial using an ion beam having a second smaller beam diameter suitable for precision milling, said high precision fiducial having at least one axis substantially parallel to the desired final edge of the sample to be extracted;
    determining the edge positions for the desired sample with respect to said axis; and
    thinning the sample section from both the first and second sides leaving a thinned sample less than 500 nm thick.

12. The method of claim 11 in which the remaining thinned sample is less than 100 nm thick.

13. The method of claim 11 in which thinning the sample section from both the first and second sides comprises:
    using image recognition to locate the edges of the vertical layer of material;
    thinning the first side of the sample by milling away material within an area beginning at half the desired sample thickness away from the center of the vertical layer of material and extending toward the first side of the sample;
    thinning the second side of the sample by milling away material within an area beginning at half the desired sample thickness away from the center of the vertical layer of material and extending toward the second side of the sample.

14. The method of claim 13 in which thinning a side of the sample comprises:
    directing a substantially normal ion beam at one side of the sample section in a milling pattern that thins the sample section in a series of passes, each pass comprising moving the beam in a raster pattern from the outside of the sample section inward to the desired sample face and then returning to the outside of the sample section, the series of passes continuing until the sample section has been thinned to a desired depth.

15. The method of claim 14 wherein moving the beam in a raster pattern from the outside of the sample section inward to the desired sample face and then returning to the outside of the sample section comprises moving the beam in a raster pattern having an x-direction parallel to the desired sample face and a y-direction perpendicular to the desired sample face, said raster pattern comprising scanning the beam back and forth in the x-direction and then stepping the beam forward toward the desired sample face, said steps continuing until the desired sample face is reached.

16. The method of claim 15 wherein the beam dwell time increases as the beam approaches the desired sample face.

17. The method of claim 11 in which thinning the sample section comprises thinning a central portion of the sample, leaving thicker material at the bottom and sides of the thinned portion.

18. The method of claim 11 in which real time pattern recognition is be used to position the ion beam and to endpoint the milling when the sample reaches a desired thickness.

19. The method of claim 11 further comprising imaging the sample section with an electron beam during the thinning process and using automatic metrology software to determine whether the desired sample thickness has been reached.

20. A system for extracting a sample from a substrate, comprising:
    a sample stage for supporting the substrate;
    an ion beam source for producing an ion beam to mill a substrate; and
    a controller programmed to control the ion beam source and the stage to carry out the method of claim 1.

21. A method of preparing two or more samples for TEM analysis for extraction from a substrate, the method comprising:
    locating a first sample site on the substrate surface;
    imaging the first sample site;
    identifying one or more desired fiducial locations for said first sample site;
    creating at least one fiducial mark for said first sample site;
    locating a second sample site on the substrate surface;
    using pattern recognition to identify at least one second fiducial location for said second sample site so that the spatial relationships between said second fiducial location and said second sample site will be identical to the spatial relationships between said first fiducial location and said first sample site;
    automatically creating a fiducial mark at the identified at least one second fiducial location;
    determining the edge positions for the desired samples to be extracted with respect to said fiducial marks;
    milling the wafer surface on either side of the desired sample locations leaving a thin layer of material containing the samples to be extracted;
    separating the samples from the substrate; and
    extracting the samples.

22. The method of claim 21 further comprising:
    after milling the wafer surface on either side of a desired sample location leaving a thin layer of material, imaging the sample site;
    using automated metrology software to determine the thickness of the thin layer of material;
    if analysis of the image determines that the layer is thicker than the desired thickness, milling the wafer surface to thin the layer; and
    repeating these steps until the desired thickness is reached.

23. The method of claim 21 in which identifying one or more desired fiducial locations for a sample site comprises
    selecting a precise fiducial location with respect to the location of a structure on the wafer surface at the sample site;
    imaging the sample site; and
    using pattern recognition software to locate the structure and determine the precise fiducial location.

24. The method of claim 21 in which identifying one or more desired fiducial locations for a sample site comprises identifying a desired fiducial location for at least one high precision fiducial mark, said high precision fiducial mark having at least one axis substantially parallel to the desired final edge of the sample to be extracted, and at least one low precision fiducial mark, said low precision fiducial mark comprising a larger fiducial mark which is recognizable in an image of the sample produced by an ion beam scan at a lower resolution suitable for bulk milling.

25. The methods of claim 21 in which at least one fiducial mark is milled on the sample to be extracted.

* * * * *